US 8,524,969 B2

(12) United States Patent
Butler et al.

(10) Patent No.: US 8,524,969 B2
(45) Date of Patent: Sep. 3, 2013

(54) DEHYDROGENATION REACTIONS OF HYDROCARBONS TO ALKENES

(75) Inventors: James Butler, League City, TX (US);
Olga Khabashesku, Houston, TX (US);
James T. Merrill, Morgan, TX (US)

(73) Assignee: Fina Technology, Inc., Houston, TX (US)

(*) Notice: Subject to any disclaimer, the term of this patent is extended or adjusted under 35 U.S.C. 154(b) by 765 days.

(21) Appl. No.: 12/506,317

(22) Filed: Jul. 21, 2009

(65) Prior Publication Data
US 2010/0022817 A1 Jan. 28, 2010

Related U.S. Application Data

(63) Continuation-in-part of application No. 12/177,740, filed on Jul. 22, 2008.

(51) Int. Cl.
*C07C 5/333* (2006.01)

(52) U.S. Cl.
USPC ........... 585/629; 585/601; 585/616; 585/627; 585/654; 585/661

(58) Field of Classification Search
USPC ............. 585/601, 616, 627, 629, 654, 661
See application file for complete search history.

(56) References Cited

U.S. PATENT DOCUMENTS

| | | | |
|---|---|---|---|
| 3,364,277 A * | 1/1968 | Siem | 585/631 |
| 3,565,969 A | 2/1971 | Hutto et al. | |
| 3,751,510 A | 8/1973 | Spoerke | |
| 3,925,498 A | 12/1975 | Stadig | |
| 4,045,419 A | 8/1977 | Winnick | |
| 4,091,046 A | 5/1978 | Dixon | |
| 4,128,708 A | 12/1978 | Liakumovich | |
| 4,147,736 A | 4/1979 | Gokhberg et al. | |
| 4,595,788 A | 6/1986 | Yamamoto et al. | |
| 4,822,936 A | 4/1989 | Maurer et al. | |
| 5,156,816 A | 10/1992 | Butler et al. | |
| 5,171,914 A * | 12/1992 | Hamilton, Jr. | 585/444 |
| 5,756,207 A | 5/1998 | Clough et al. | |
| 5,962,757 A * | 10/1999 | Milam et al. | 585/444 |
| 6,066,705 A | 5/2000 | Calderon | |
| 6,166,280 A | 12/2000 | Rubini et al. | |
| 6,747,181 B1 | 6/2004 | Bosman et al. | |
| 6,762,335 B1 | 7/2004 | Prince et al. | |
| 7,105,711 B2 | 9/2006 | Merrill | |
| 7,157,533 B2 | 1/2007 | Gandon-Pain | |
| 2005/0119515 A1 | 6/2005 | Machhammer et al. | |
| 2006/0106267 A1* | 5/2006 | Kowaleski | 585/444 |
| 2006/0106268 A1* | 5/2006 | Kowaleski | 585/444 |
| 2006/0106269 A1* | 5/2006 | Culp et al. | 585/444 |
| 2007/0099299 A1 | 5/2007 | Simon et al. | |
| 2007/0167661 A1 | 7/2007 | Johann et al. | |

(Continued)

OTHER PUBLICATIONS

Lide, et al., CRC Handbook of Chemistry and Physics, 91st edition, 2011 Internet edition.*

(Continued)

*Primary Examiner* — In Suk Bullock
*Assistant Examiner* — Bradley Etherton

(57) ABSTRACT

A method for the dehydrogenation of hydrocarbons to alkenes, such as n-pentene to piperylene and n-butane to butadiene at pressures less than atmospheric utilizing a dehydrogenation catalyst are disclosed. Embodiments involve operating the dehydrogenation reactor at a pressure of 1,000 mbar or less.

12 Claims, 4 Drawing Sheets

(56) References Cited

U.S. PATENT DOCUMENTS

| | | |
|---|---|---|
| 2007/0179330 A1 | 8/2007 | Johann et al. |
| 2008/0119680 A1 | 5/2008 | Crone et al. |
| 2009/0318741 A1* | 12/2009 | Newman ...................... 585/440 |
| 2010/0022816 A1* | 1/2010 | Merrill ......................... 585/661 |
| 2010/0099936 A1 | 4/2010 | Shin et al. |

OTHER PUBLICATIONS

Note: The Present Application Is a Continuation-In-Part of U.S. Appl. No. 12/177,740, filed Jul. 22, 2008.

Xi Liu, et al.; "Oxidative Dehydrogenation of 1-butene to Butadiene Over Carbon Nanotube Catalysts"; Carbon 46 (2008); pp. 547-549.

* cited by examiner

DEHYDROGENATION REACTIONS OF HYDROCARBONS TO ALKENES

CROSS-REFERENCE TO RELATED APPLICATIONS

This application is a continuation-in-part of U.S. patent application Ser. No. 12/177,740 filed on Jul. 22, 2008.

FIELD

The present invention generally relates to the dehydrogenation of hydrocarbons to form alkenes such as isoprene, piperylene and butadiene.

BACKGROUND

Isoprene is the common name for the chemical compound known as 2-methyl-buta-1,3-diene, that is found in natural rubber. Isoprene is used as a starting material for the production of synthetic versions of natural rubber including polyisoprene and various isoprene-based rubbery copolymers such as styrene-butadiene type copolymers. Isoprene can be produced using a variety of processes. These can include, for example, byproducts of various refining operations such as the thermal cracking of naphtha or oil; the dehydrogenation of isoamylene compounds; the pyrolysis of allylic esters; and the decomposition of dioxane.

Isoamylene may be a component of a $C_5$ refinery stream. The isoamylene portion of such a stream will typically contain at least two isoamylene monomers, i.e., 2-methyl-2-butene and 2-methyl-1-butene, often in a weight ratio of about 1:1 to about 10:1, and most often between 1:1 and 5:1, respectively. A third monomer, 3-methyl-1-butene may also be present but is typically in much lower amounts than the other two monomers. Isoprene can be produced by the catalytic dehydrogenation reaction of isoamylene in the presence of oxygen. The oxygen is typically provided by adding steam to the reaction zone.

N-pentene, also referred to as 1-pentene, is an alpha-olefin. N-Pentene is commonly made as a byproduct of catalytic or thermal cracking of petroleum, or during production of ethylene and propylene via thermal cracking of hydrocarbon fractions. N-pentene is rarely isolated as a separate compound. Instead, it is often blended into gasoline, or blended into a mixture with other hydrocarbons, which is alkylated with isobutane to make gasoline.

Piperylene, also known as 1,3-pentadiene, is commonly produced as part of the separation process when separating crude C5 compounds from pyrolysis gasoline. Piperylene may also be obtained from crude oil. However, obtaining piperylene from crude oil generally requires a number of extraction steps. Piperylene is used as an intermediate monomer in the manufacture of plastics, adhesives and resins. Products obtained from piperylene monomers are commonly present in adhesives, such as those used in the manufacture of tapes and envelopes.

N-butane, sometimes called simply "butane" is an unbranched alkane of four carbon atoms. N-butane gas is sold bottled as a fuel for cooking and camping. N-butane is also used as a petrol component and as a feedstock for the production of base petrochemicals in steam cracking. When n-butane is blended with propane and other hydrocarbons, it is referred to commercially as LPG.

Butadiene, also known as 1,3-butadiene, is a common monomer is the production of synthetic rubber. Butadiene is commonly produced as a by-product in the steam cracking processes used to produce ethylene and other olefins. Butadiene may also be produced by the dehydrogenation of n-butanes.

It may be desirable to utilize equipment that has the capability of producing more than a single product. For example, it may be beneficial to have the ability to utilize equipment typically used for the dehydrogenation of ethylbenzene to styrene also for the dehydrogenation of isoamylene to isoprene. It may be desirable to utilize commercial catalysts that are typically used for dehydrogenation reactions such as ethylbenzene to styrene reactions for the dehydrogenation of other hydrocarbons to alkenes, such as isoamylene to isoprene, pentene to piperylene, or n-butane to butadiene.

Efforts to utilize commercial catalysts that are typically used in ethylbenzene to styrene reactions for the dehydrogenation of isoamylene to isoprene have required high steam-to-hydrocarbon ratios and resulted in relatively short catalyst life. The higher steam-to-hydrocarbon ratio will increase the operating cost due to the need for more steam, therefore having an adverse effect on the economics of the process. Further, due to the decrease of catalyst activity, steaming of the catalyst is required in a regeneration step to restore activity. The operation of steaming the catalyst has a detrimental economic effect from the increased steam required and the reduction in product produced during this regeneration operation. The repeated action of steaming the catalyst typically results in a decrease in the useful life of the catalyst.

It may be desirable to be able to utilize equipment and catalysts typically used to dehydrogenate ethylbenzene to styrene also for the dehydrogenation of other hydrocarbons to alkenes, such as isoamylene to isoprene, n-pentene to piperylene and/or n-butane to butadiene in a method that exhibits increased catalyst life with a reduction in the need for catalyst steaming.

SUMMARY

Embodiments of the present invention generally include a method for producing alkenes from the dehydrogenation of hydrocarbons in a reactor. The hydrocarbon feedstock and steam are contacted with a dehydrogenation catalyst within the reactor under conditions effective to dehydrogenate at least a portion of the hydrocarbons to produce alkenes. In an embodiment, the reactor is operated under a vacuum at a pressure of 1,000 mbar or less. A product is recovered from the dehydrogenation reactor containing alkenes.

Embodiments of the present invention include a method for producing piperylene by supplying a hydrocarbon feedstock containing n-pentene to a dehydrogenation reactor. The hydrocarbon feedstock and steam are contacted with a dehydrogenation catalyst within the reactor under conditions effective to dehydrogenate at least a portion of the n-pentenes to produce piperylene. In an embodiment, the reactor is operated under a vacuum at a pressure of 1,000 mbar or less. A product is recovered from the dehydrogenation reactor containing piperylene. Another embodiment includes producing butadiene by supplying a hydrocarbon feedstock containing n-butane.

The methods can further include supplying steam to the dehydrogenation reactor in a steam to hydrocarbon molar ratio of at least 10:1 and operating the dehydrogenation reactor at a temperature of at least 300° C. The conversion of n-pentene to piperylene can be at least 30%. The conversion of n-butane to butadiene can be at least 30%.

In an aspect, the dehydrogenation catalyst has an average effective pore diameter of at least 500 nanometers and has ferric oxide as a major component and potassium as a lesser component. In an embodiment, the dehydrogenation catalyst contains ferric oxide in amounts ranging from 40 wt % to 80 wt % and potassium oxide or potassium carbonate in an amount of about 5 wt % to 30 wt %.

The methods can further include operating the dehydrogenation reactor at a steam to hydrocarbon molar ratio of at least 12:1, increasing the reactor temperature as needed to keep the conversion at least 35%, and where such catalyst deactivation during the dehydrogenation averages no more than 1° C. per day.

In another embodiment, the dehydrogenation reactor is operated at a steam to hydrocarbon molar ratio of at least 15:1 and at a pressure of 350 mbar or less. The reactor temperature is increased as needed to keep the conversion at least 40 wt %, and where such catalyst deactivation during the dehydrogenation averages no more than 0.5° C. per day.

In an embodiment the reactor and reactions are operable at least 30 days before the catalyst is a deactivated catalyst. In other embodiments the reactor and reactions are operable for at least 45 days, and alternatively at least for 60 days before the catalyst is a deactivated catalyst.

Still another embodiment is for a method of producing alkenes in an ethylbenzene dehydrogenation reactor containing an EB dehydrogenation catalyst. The method includes modifying a dehydrogenation reactor to enable the removal of a vapor stream from the reactor and reduce the reactor pressure to vacuum conditions of 1,000 mbar or less and supplying a hydrocarbon feedstock to the reactor and supplying steam to the dehydrogenation reactor in a steam to hydrocarbon molar ratio of at least 10:1. The hydrocarbon feedstock and steam are contacted with a dehydrogenation catalyst within the reactor which is operated at a temperature of at least 300° C. and vacuum conditions wherein substantially all of the hydrocarbons after the reactor are in a vapor phase. A vapor product is recovered from the dehydrogenation reactor.

The hydrocarbon feedstock can be at least 95 wt % n-pentene and the product can contain at least 30 wt % piperylene. Alternately the hydrocarbon feedstock can be at least 95 wt % n-butane and the product can contain at least 30 wt % butadiene.

DETAILED DESCRIPTION

Figure 1:
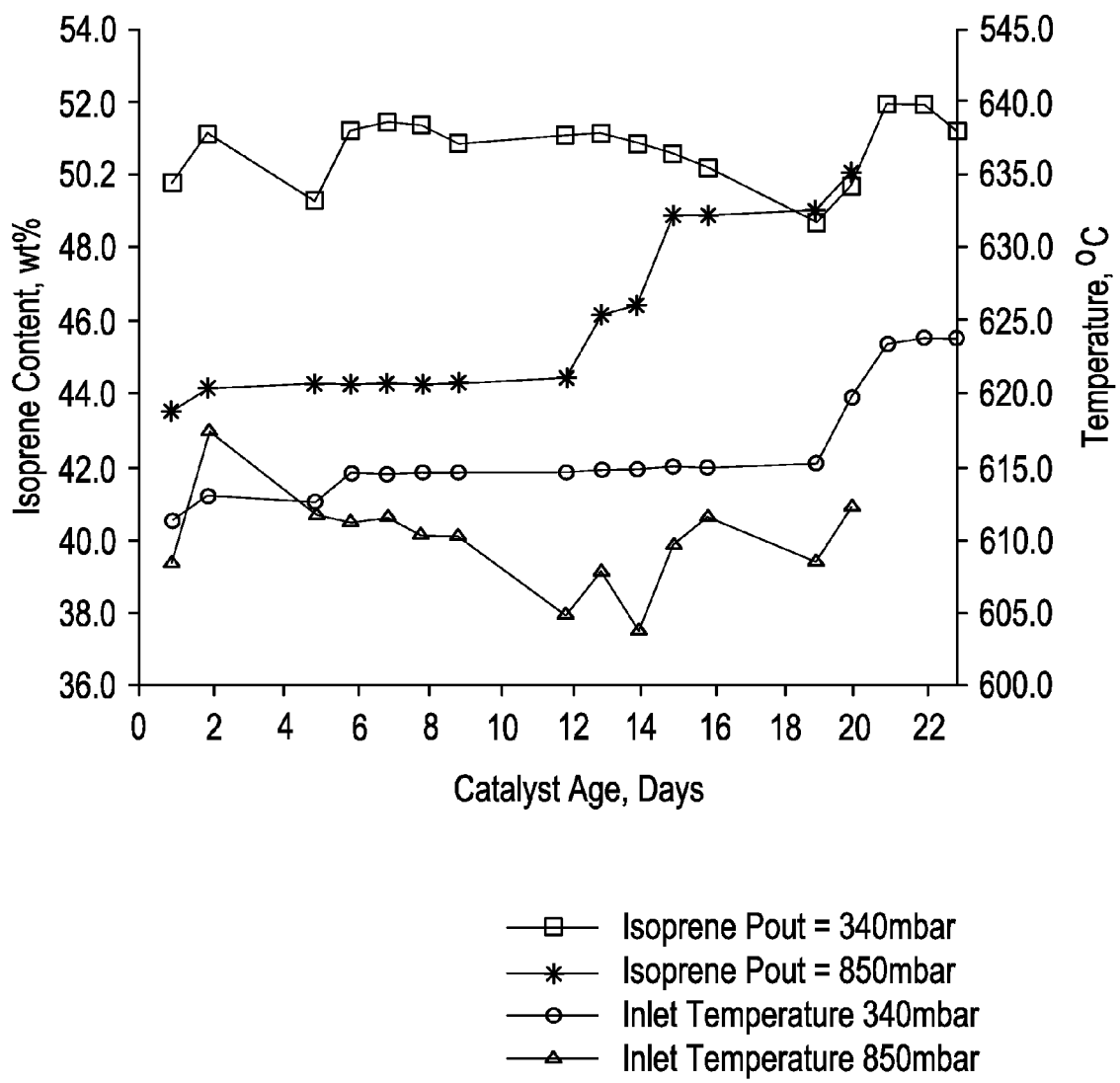
FIG. 1 illustrates results obtained from the dehydrogenation of isoamylene to isoprene at a steam to hydrocarbon molar ratio of 20:1 at pressures of 850 mbar and 340 mbar.

The present invention involves the production of alkenes by dehydrogenating a hydrocarbon containing feed. The feed is subjected to catalytic dehydrogenation under vacuum conditions that enable the dehydrogenation of the hydrocarbons to form a product having alkene content equivalent to a conversion of at least 30%. As used herein the phrase "conversion of at least xx %" means that at least xx weight percent of the particular hydrocarbon content in the feed converts to an alkene during the dehydrogenation process and is contained in the product stream.

An embodiment of the present invention involves the production of piperylene by dehydrogenating a pentene containing feed. The pentene feed is subjected to catalytic dehydrogenation under vacuum conditions that enable the dehydrogenation of the n-pentenes to form a product having piperylene content equivalent to a pentene conversion of at least 30%. In this embodiment the phrase "conversion of at least xx %" means that at least xx weight percent of the n-pentene content in the feed converts to piperylene during the dehydrogenation process and is contained in the product stream.

An embodiment of the present invention involves the production of butadiene by dehydrogenating an n-butane containing feed. The n-butane feed is subjected to catalytic dehydrogenation under vacuum conditions that enable the dehydrogenation of the n-butanes to form a product having butadiene content equivalent to an n-butane conversion of at least 30%. In this embodiment the phrase "conversion of at least xx %" means that at least xx weight percent of the n-butane content in the feed converts to butadiene during the dehydrogenation process and is contained in the product stream.

In embodiments of the dehydrogenation reaction, steam and the n-pentene and/or n-butane containing hydrocarbon feedstock can be supplied in a steam to hydrocarbon molar ratio of between 1:1 to about 25:1. The steam can be mixed with the hydrocarbon either prior to introduction to the reactor, or the steam and hydrocarbon can be supplied separately to the reactor through separate lines. The steam is condensed and forms a liquid portion, this liquid water along with any liquid hydrocarbons that may have been present in the feed or produced in the reaction, such as aromatics, for example benzene, toluene or xylene, can be drained from the reactor or a subsequent separation stage, in any suitable method. The reacted hydrocarbon can be removed as either a liquid or a vapor, depending on the reactor conditions.

Under the conditions of the present invention, substantially all of the produced alkene and unreacted hydrocarbon containing feed are vaporized and are removed in a vapor phase by any suitable method, such as a vacuum compressor, which can maintain the reactor pressure at the desired vacuum conditions.

In an embodiment there are one or more reactors, in parallel or series, wherein the catalyst is located and one or more reaction zones exist. In addition to the reactor, there may be a subsequent separation stage that enables the liquid from the reactor to be recovered and the vapor product to be removed. A heat exchanger may also be utilized to cool the reaction effluent prior to the separation stage. The operating pressure of a separation stage may be essentially the same as the outlet pressure of the reactor, other than the pressure drop that may occur across the heat exchanger. In alternate embodiments the operating pressure of a separation stage may be different than the reactor. Methods and processes of dehydrogenation disclosed in U.S. patent application Ser. No. 11/811,084 filed Jun. 8, 2007 by Merrill, incorporated by reference herein, may be suitable for embodiments of the present invention.

The dehydrogenation catalyst can be any dehydrogenation catalyst having a large enough pore size in order to avoid excessive diffusion limitations leading to restriction of the conversion of n-pentene to piperylene and n-butane to butadiene, such as for a non-limiting example, those with an average effective pore diameter of at least 300 nanometers, at least 400 nanometers, or at least 500 nanometers. Subject to the pore diameter restrictions, the dehydrogenation catalyst may be of any suitable type, such as a catalyst containing iron as a major component with a lesser amount of potassium.

In a particular application of the invention the dehydrogenation catalyst is a ferric oxide, potassium carbonate based dehydrogenation catalyst having a relatively large average pore diameter, such as a pore diameter of at least 500 nanometers. Lesser amounts of cerium and other lanthanide group rare earths may also be present. Suitable catalyst compositions may comprise ferric oxide in amounts ranging from 40 to 80 wt %, potassium oxide or potassium carbonate in an amount of about 5 to 30 wt % and may also include lesser amount of cerium, and other suitable catalyst promoters. Catalysts disclosed in U.S. patent application Ser. No. 11/811,084 filed Jun. 8, 2007 by Merrill, incorporated by reference herein, may be utilized in the present invention.

In an aspect, the catalyst may be formed by mulling the iron and potassium components with, for example, a plastic hydraulic cement binder followed by extruding the material to form catalyst particles of about from 2.5 mm to 5.0 mm in diameter having an average effective pore diameter of at least 500 nanometers. More specifically the dehydrogenation catalyst may have an average effective pore diameter of at least 550 nanometers and may have an average effective pore diameter of between 550 nanometers and 2,000 nanometers.

The dehydrogenation catalyst can be, by non-limiting example: Styromax Plus from Sud-Chemie or Hypercat GV from Criterion.

In the present invention the LHSV can be any flow rate wherein the subject reaction can be achieved; such as for example embodiments of the invention can range from 0.1 hr$^{-1}$ to 10.0 hr$^{-1}$, or from 0.1 hr$^{-1}$ to 5.0 hr$^{-1}$.

During the experiments the steam-to-hydrocarbon molar ratio was varied from 20:1 to 16:1 and the reactor pressure was varied from 850 mbar to 290 mbar. Suitable steam-to-hydrocarbon molar ratio for embodiments of the invention can range from 10:1 to 30:1 or from 10:1 to 20:1. Suitable reactor pressure for the invention can range from 100 mbar to 1000 mbar and in particular embodiments can range from 200 mbar to 900 mbar.

Suitable reaction temperature for the invention can range from 300° C. to 800° C.

EXPERIMENTAL EXAMPLES

Experiments 1 through 6 were performed in which a dehydrogenation catalyst, such as those used for the conversion of ethylbenzene to styrene, was used for the reaction of isoamylene to isoprene. Catalysts that were tested are commercially available and included Styromax Plus from Sud-Chemie and Hypercat GV from Criterion. Other commercially available dehydrogenation catalysts were also tested with comparable results. The feed composition for the experiments was a mixture of about 93.8% 2-methyl-2-butene and about 6.2% 2-methyl-1-butene. In each of the experiments the flow rate of the input hydrocarbon stream was set at a LHSV of 0.35 hr$^{-1}$. During the various experimental runs the reaction temperature was adjusted at times in an effort to maintain a somewhat constant isoprene content in the product. The term "reaction temperature" as used herein refers to the reactor inlet temperature unless otherwise noted.

Experiment 1

In Experiment #1 a steam-to-hydrocarbon molar ratio of 20:1 was used at a pressure of 850 mbar. The catalyst used was Styromax Plus from Sud-Chemie, which is a commercially available dehydrogenation catalyst. The results are shown in FIG. 1 wherein a product having an isoprene content of about 38 wt % to about 41 wt % was produced with a temperature starting at about 619° C. and rising to about 635° C. after 20 days. In the course of carrying out the dehydrogenation reaction, the catalyst becomes progressively deactivated resulting in a decrease in the isoprene content of the product and requiring the temperature to be steadily increased to maintain conversion. There was a cumulative increase of the reaction temperature of 15° C. that was observed over the 20 days of Experiment #1. The reactor temperature increase from catalyst deactivation averaged less than 1° C. per day over the isoamylene to isoprene dehydrogenation run.

The experimental results illustrate that a dehydrogenation catalyst that is typically used in the reaction of ethylbenzene to styrene can be used for the dehydrogenation of methylbutene to isoprene at a pressure of approximately 850 mbar or less, a steam-to-hydrocarbon molar ratio of at least 20:1, and can achieve sufficient conversion to produce a product having an isoprene content of at least 35 wt %. In this embodiment an average temperature increase of about 0.75° C. per day was observed over the isoamylene to isoprene dehydrogenation run.

The following table gives experimental data from Experiment 1.

| Day | Press mbar | Temp ° C. | SHR | Isoprene wt % |
|---|---|---|---|---|
| 1 | 850 | 618.9 | 20 | 39.5 |
| 2 | 850 | 620.5 | 20 | 43 |
| 5 | 850 | 620.7 | 20.1 | 40.8 |
| 6 | 850 | 620.8 | 20 | 40.6 |
| 7 | 850 | 620.8 | 20 | 40.7 |
| 8 | 850 | 620.8 | 20 | 40.2 |
| 9 | 850 | 620.9 | 20 | 40.2 |
| 12 | 850 | 621.2 | 20 | 38 |
| 13 | 850 | 625.6 | 19.9 | 39.2 |
| 14 | 850 | 626.1 | 20 | 37.6 |
| 15 | 850 | 632.2 | 18.8 | 40 |
| 16 | 850 | 632.3 | 20 | 40.7 |
| 19 | 850 | 632.7 | 20.1 | 39.5 |
| 20 | 850 | 635.3 | 20 | 41 |
| 21 | 850 | 626.4 | 14.4 | 32.8 |
| 22 | 850 | 640.9 | 14.3 | 34 |
| 26 | 850 | 625.5 | 17.3 | 27.8 |
| 27 | 850 | 631.1 | 17.3 | 39.1 |
| 28 | 850 | 630.8 | 17.3 | 45.5 |
| 31 | 850 | 632.5 | 17.4 | 37.1 |
| 32 | 850 | 639.1 | 17.3 | 56.5 |
| 33 | 850 | 629.8 | 17.4 | 41.1 |
| 34 | 850 | 636.7 | 17.4 | 35.7 |
| 35 | 849.9 | 630.1 | 17.3 | 40.4 |
| 39 | 850 | 640.5 | 17.4 | 35.8 |
| 40 | 850 | 630.6 | 17.4 | 34.1 |
| 41 | 850 | 631.7 | 17.4 | 35.7 |
| 42 | 850 | 638 | 19.4 | 40.8 |
| 43 | 850 | 638.2 | 19.4 | 40 |
| 44 | 850 | 638.1 | 19.5 | 38.3 |
| 47 | 850 | 638.6 | 19.4 | 37.5 |

Experiment #2

In Experiment #2 operating conditions of a steam-to-hydrocarbon molar ratio of 20:1 was used at a pressure of 340 mbar. The catalyst used was Sud-Chemie Styromax Plus. The results are shown in FIG. 1 wherein a product having an isoprene content of about 49 wt % to about 52 wt % was produced with a temperature starting at about 611° C. and rising to about 624° C. after 23 days. In the course of carrying out the dehydrogenation reaction, the catalyst showed some deactivation requiring the temperature to be increased on days 20 and 21 to maintain isoprene content above 50 wt %. A total of a 13° C. increase in the reaction temperature was observed over the 23 days of Experiment #2.

The experimental results shown in FIG. 1 illustrate that reducing the pressure results in an increase in conversion at a consistent steam-to-hydrocarbon molar ratio, in Experiment #2 pressure reduction from approximately 850 mbar to approximately 340 mbar can result in an increase in conversion to produce a product having an increased isoprene content, in this case of at least 45 wt % at the same steam-to-hydrocarbon molar ratio of 20:1. This increase in conversion is found to occur at a reduced temperature. In this embodiment an average temperature increase from catalyst deactivation of about 0.5° C. per day was observed over the isoamylene to isoprene dehydrogenation run.

Experiment #3

Figure 2:
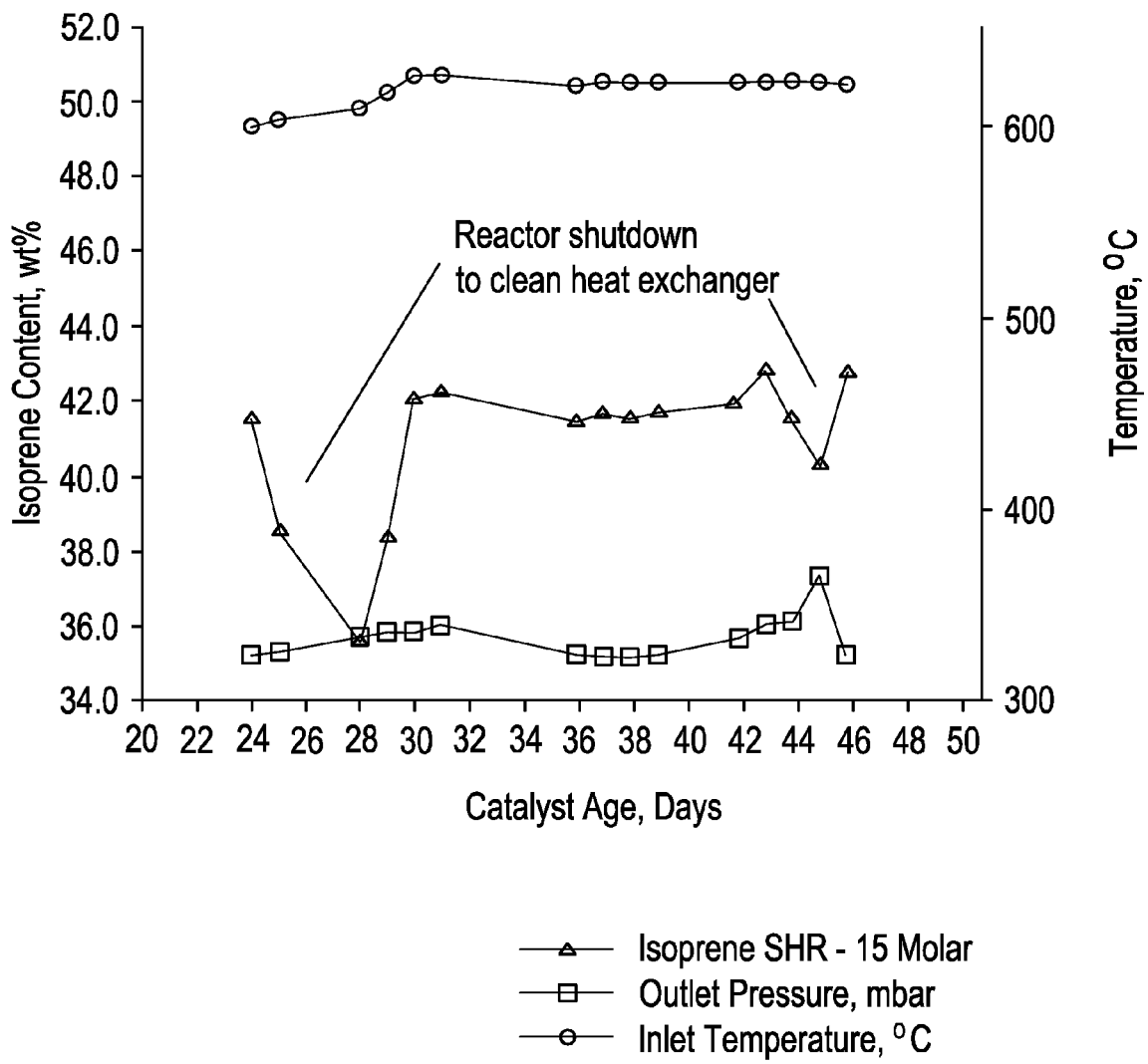
FIG. 2 illustrates results obtained from the dehydrogenation of isoamylene to isoprene at a steam to hydrocarbon molar ratio of 15:1 at a pressure of 340 mbar.

In Experiment #3 the reaction from Experiment #2 was continued although with a reduced steam-to-hydrocarbon molar ratio of 15:1 at the pressure of approximately 340 mbar. The results are shown in FIG. 2 wherein a product having an isoprene content of about 36 wt % to about 43 wt % was produced with a reaction temperature starting at about 600° C. on day 24 and ending at about 622° C. on day 46 for an overall 22° C. increase over the 22 day run. An initial temperature rise of 26° C. occurred in the first seven days, which then decreased to a temperature rise of about 22° C. and stabilized at a reaction temperature of about 622° C. over the remaining 15 days of Experiment #3.

Reducing the steam-to-hydrocarbon molar ratio from 20:1 to 15:1 resulted in a corresponding reduction in the isoprene content of the product, in these experiments from about 50 wt % to about 42 wt %. In Experiment #3 an average temperature increase of about 1.0° C. per day was observed over the experimental run, although no significant temperature rise was observed during the final ten days of the experimental run, indicating a steady-state operation without significant catalyst deactivation.

Experiment #4

Figure 3:
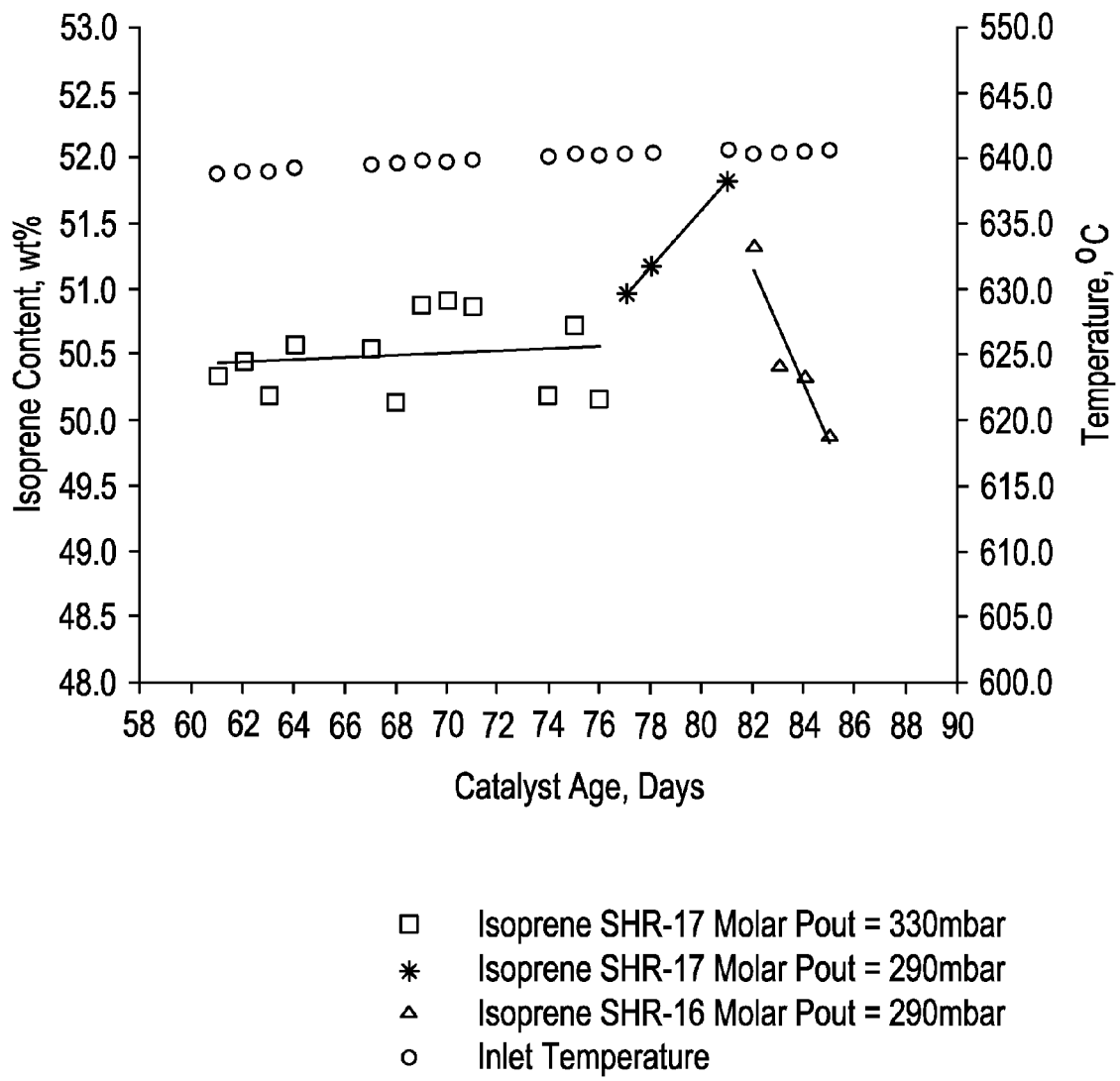
FIG. 3 illustrates results obtained from the dehydrogenation of isoamylene to isoprene at steam to hydrocarbon molar ratios of 17:1 and 16:1 at pressures of 330 mbar and 290 mbar.

In Experiment #4 the reaction from Experiments #2 and #3 was continued although with an increased steam-to-hydrocarbon molar ratio of 17:1 at a pressure of approximately 330 mbar. The results are shown in FIG. 3 wherein a product having an isoprene content of about 50 wt % to about 51 wt % was produced with a temperature starting at about 639° C. on day 61 and rising to about 641° C. on day 76. A 2° C. increase was observed over the 15 days of Experiment #4. Experiment #4 showed a stable reaction at a steam-to-hydrocarbon molar ratio of 17:1 and a pressure of 330 mbar while producing a product of slightly more than 50 wt % isoprene.

Increasing the steam-to-hydrocarbon molar ratio from 15:1 to 17:1 resulted in maintaining a stable reaction producing a product having an increased isoprene content of approximately 50 wt %. In this experiment an average temperature increase from catalyst deactivation of less than 0.2° C. per day was observed. The slight rise in temperature can also be seen to correspond with a slight increase of isoprene content in the product, indicating steady-state operation with stable conversion without significant catalyst deactivation.

Experiment #5

In Experiment #5 the experimental conditions and reaction of Experiment #4 was continued with a steam-to-hydrocarbon molar ratio of 17:1, except that the pressure was reduced to 290 mbar. The results are shown in FIG. 3 wherein the isoprene content increased to 51 wt % on day 77 and further increased to almost 52 wt % on day 81 while the temperature increased by only 0.1° C. over these days. Experiment #5 illustrates the benefit of reduced reaction pressure on the conversion of methylbutenes to isoprene to produce a product with increased isoprene content without significant catalyst deactivation. This experiment demonstrated a stable reaction at a steam-to-hydrocarbon molar ratio of 17:1 and a pressure of 290 mbar while producing a product of greater than 50 wt % isoprene.

Reducing the pressure to approximately 290 mbar while maintaining a steam-to-hydrocarbon molar ratio of 17:1 resulted in maintaining a stable reaction of product having an isoprene content of more than 50 wt %. In this embodiment an average temperature increase from catalyst deactivation of about 0.025° C. per day was observed.

Experiment #6

In Experiment #6 the reaction of Experiment #5 was continued with a pressure of 290 mbar although the steam-to-hydrocarbon molar ratio was reduced to 16:1. The results are shown in FIG. 3 wherein the isoprene content showed a decreasing trend from 51.4 wt % on day 82 to about 49.9 wt % on day 85 while the temperature remained steady. Experiment #6 illustrates that a reduction in steam-to-hydrocarbon molar ratio from 17:1 to 16:1 and constant pressure will result in decreasing isoprene content, which was expected.

Reducing the steam-to-hydrocarbon molar ratio to 16:1 at the steady pressure of approximately 290 mbar exhibited a decreasing trend in the isoprene content in the product of approximately 0.5 wt % per day during the four days of the experiment. The decrease in conversion may possibly have been overcome by an increase in the reactor temperature. It is also possible that the isoprene content may have stabilized at a level between 40 wt % and 50 wt % if the reaction had been allowed to continue. In experiment #3 with a steam-to-hydrocarbon molar ratio of 15:1 at 340 mbar the isoprene content in the product was about 42 wt %; therefore at a steam-to-hydrocarbon molar ratio of 16:1 at 290 mbar the isoprene content in the product would be expected to be greater than 42 wt %. Also of note is that at this point in the experiments the catalyst had been in continuous service for over 80 days and had been subjected to the many changing conditions described above, thereby possibly having some lack of activity and selectivity due to the extended run.

The following table gives experimental data from Experiments 2 through 6.

| Day | Press mbar | Temp ° C. | SHR | Isoprene wt % |
|---|---|---|---|---|
| 1 |  | 611.4 | 20 | 49.8 |
| 2 | 343 | 613.1 | 20 | 51.1 |
| 5 | 431 | 612.7 | 20 | 49.3 |
| 6 | 335 | 614.6 | 20 | 51.2 |
| 7 | 335 | 614.5 | 20 | 51.4 |
| 8 | 335 | 614.7 | 20 | 51.4 |
| 9 | 335 | 614.7 | 20 | 50.9 |
| 12 | 337 | 614.7 | 20 | 51.1 |
| 13 | 339 | 614.9 | 20 | 51.2 |
| 14 | 337 | 614.9 | 20 | 50.9 |
| 15 | 338 | 615 | 20 | 50.6 |
| 16 | 338 | 615 | 20 | 50.2 |
| 19 | 346 | 615.3 | 20 | 48.7 |
| 20 | 355 | 619.8 | 20 | 49.7 |
| 21 | 355 | 623.5 | 20 | 51.9 |
| 22 | 363 | 623.8 | 20 | 51.9 |
| 23 | 369 | 623.9 | 20 | 51.2 |
| 24 | 324 | 599.2 | 20 | 41.5 |
| 25 | 325 | 602.6 | 15 | 38.6 |
| 28 | 334 | 607.8 | 15 | 35.6 |
| 29 | 335 | 616.7 | 15 | 38.4 |
| 30 | 335 | 625.6 | 15 | 42.1 |
| 31 | 338 | 626 | 15 | 42.3 |
| 36 | 324 | 621.1 | 15 | 41.6 |
| 37 | 322 | 621.7 | 15 | 41.7 |
| 38 | 323 | 621.8 | 15 | 41.6 |
| 39 | 323 | 621.9 | 15 | 41.7 |

-continued

| Day | Press mbar | Temp ° C. | SHR | Isoprene wt % |
|---|---|---|---|---|
| 42 | 332 | 622 | 15 | 41.9 |
| 43 | 339 | 622.2 | 15 | 42.9 |
| 44 | 341 | 622.3 | 15 | 41.6 |
| 45 | 365 | 622.4 | 15 | 40.4 |
| 46 | 323 | 621.6 | 15 | 42.8 |
| 49 | 336 | 626.5 | 20 | 51.1 |
| 50 | 330.3 | 627 | 20 | 50.7 |
| 53 | 357.3 | 630.1 | 20 | 50.8 |
| 54 | 339.4 | 625.3 | 20.3 | 50.7 |
| 55 | 343.8 | 625.4 | 20.3 | 50.3 |
| 56 | 338.3 | 631 | 17 | 49.4 |
| 57 | 354.7 | 634.5 | 17 | 49.7 |
| 60 | 350.4 | 638.7 | 17 | 50.7 |
| 61 | 353 | 638.8 | 17 | 50.3 |
| 62 | 330.6 | 639 | 17 | 50.4 |
| 63 | 341.4 | 639.1 | 17 | 50.2 |
| 64 | 329.2 | 639.3 | 17 | 50.6 |
| 67 | 326.9 | 639.5 | 17 | 50.5 |
| 68 | 344.2 | 639.7 | 17 | 50.2 |
| 69 | 321.1 | 639.8 | 17 | 50.9 |
| 70 | 328.2 | 639.9 | 17 | 50.9 |
| 71 | 317.4 | 639.9 | 17 | 50.9 |
| 74 | 349.4 | 640.2 | 17 | 50.2 |
| 75 | 347.1 | 640.3 | 17 | 50.7 |
| 76 | 334.1 | 640.3 | 17 | 50.2 |
| 77 | 296 | 640.4 | 17 | 51 |
| 78 | 273.1 | 640.5 | 17 | 51.2 |
| 81 | 297.2 | 640.7 | 17 | 51.8 |
| 82 | 292.1 | 640.4 | 16 | 51.3 |
| 83 | 292.1 | 640.5 | 16 | 50.4 |
| 84 | 285.2 | 640.6 | 16 | 50.3 |
| 85 | 283.1 | 640.7 | 16 | 49.9 |

Experiment #7

Figure 4:
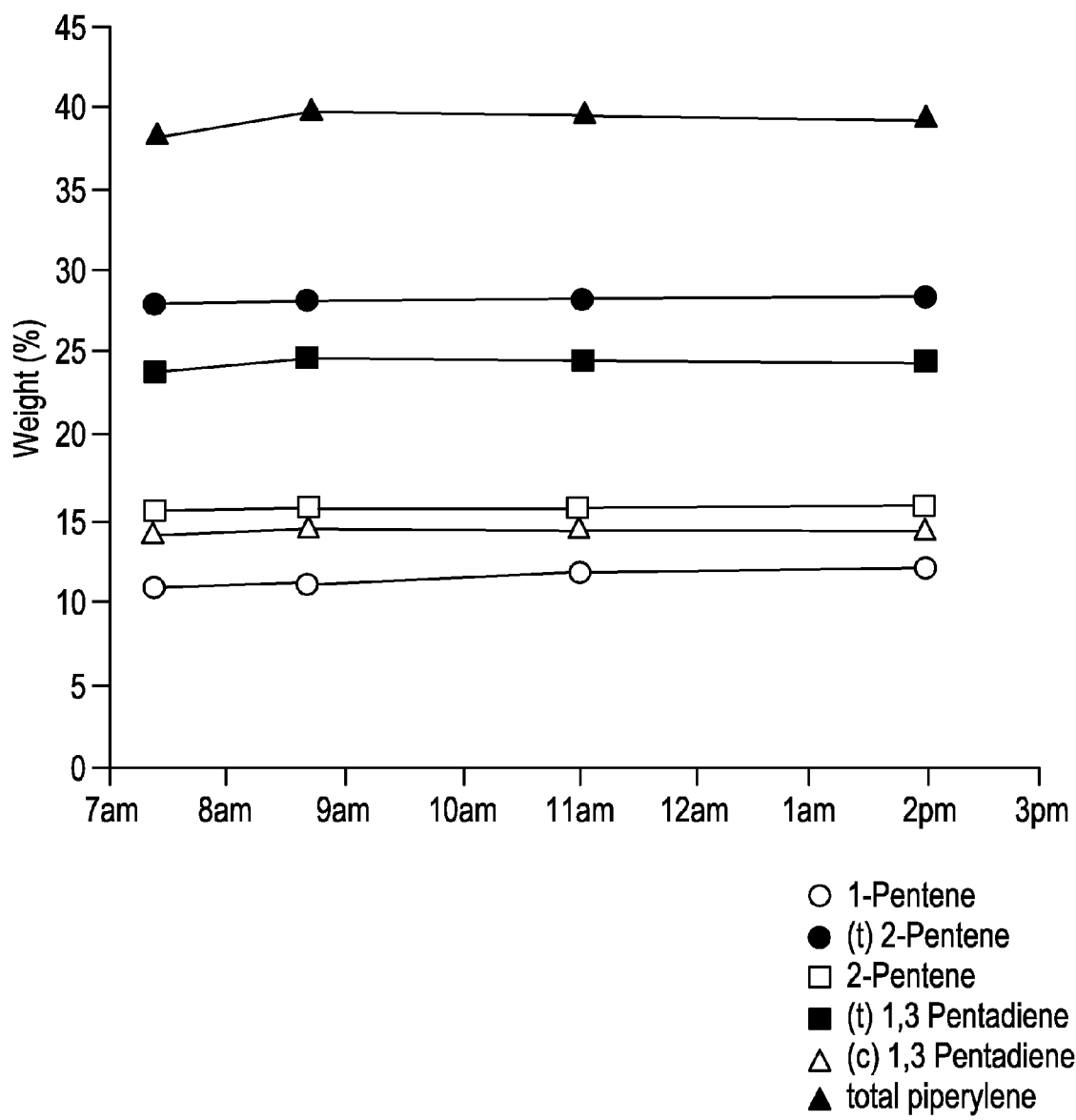
FIG. 4 illustrates results obtained from the dehydrogenation of pentene to piperylene at a stream to hydrocarbon molar ratio of 22.4:1 and a pressure of 286 mbar.

In Experiment #7 a hydrocarbon feed containing pentene was introduced to achieve a product containing piperylene, wherein the feed had an n-pentene content of about 98.83 wt %. A steam-to-hydrocarbon molar ratio of 22.4:1 was used at a pressure of 286 mbar. The LHSV was 0.31. The catalyst used was Styromax Plus from Sud-Chemie, which is a commercially available dehydrogenation catalyst. The results are shown in FIG. 4 wherein a product having a piperylene, 1,3 pentadiene (cis and trans), content of about 37.94 wt % to about 39.03 wt % was produced with a temperature of about 590.8° C.

The following gives experimental data from Experiment 7.

|  | Sample | | | |
|---|---|---|---|---|
|  | 1 | 2 | 3 | 4 |
| Conditions | | | | |
| Press Mbar | 286 | 286 | 286 | 286 |
| Temp ° C. | 590.8 | 590.8 | 590.8 | 590.8 |
| LHSV | 0.31 | 0.31 | 0.31 | 0.31 |
| SHR | 22.4 | 22.4 | 22.4 | 22.4 |
| Feed content Wt % | | | | |
| N-Pentene | 98.83 | 98.83 | 98.83 | 98.83 |
| Product content Wt % | | | | |
| Piperylene | 37.94 | 39.03 | 38.79 | 38.47 |
| cis | 13.98 | 14.43 | 14.34 | 14.17 |
| trans | 23.96 | 24.59 | 24.45 | 24.30 |
| 2-pentene (t) | 28.08 | 28.07 | 27.98 | 28.29 |
| 2-pentene (c) | 15.79 | 15.96 | 15.93 | 16.05 |
| 1-pentene | 11.66 | 11.82 | 12.04 | 12.14 |

Various terms are used herein, to the extent a term used in not defined herein, it should be given the broadest definition persons in the pertinent art have given that term as reflected in printed publications and issued patents.

The term "activity" refers to the weight of product produced per weight of the catalyst used in a process per hour of reaction at a standard set of conditions (e.g., grams product/gram catalyst/hr).

The term "conversion" refers to the weight percent of a component in the feed that converts to a new component in the product stream during the dehydrogenation process.

The term "deactivated catalyst" refers to a catalyst that has lost enough catalyst activity to no longer be efficient in a specified process. Such efficiency is determined by individual process parameters.

The term "EB dehydrogenation catalyst" refers to a catalyst that has the capability to catalyze the dehydrogenation reaction of ethylbenzene to styrene. The EB dehydrogenation catalyst is not limited to a commercially available catalyst or one that is commercially used for the dehydrogenation of ethylbenzene to styrene. The term EB dehydrogenation catalyst would include those catalysts that are in commercial use for the dehydrogenation reaction of ethylbenzene to styrene and catalysts that are commercially available for the dehydrogenation reaction of ethylbenzene to styrene.

The term "isoamylene" as used herein is meant to refer to any methylbutene in one or more of the isomeric states and in combinations thereof. The methylbutene isomers are: 2-methyl-2-butene; 2-methyl-1-butene; and 3-methyl-1-butene. Isoprene can be produced by the catalytic dehydrogenation reaction of methylbutene isomer 2-methyl-2-butene in the presence of oxygen. Upon the reaction of the 2-methyl-2-butene isomer to isoprene, the equilibrium between the isomers will be disrupted and can result in the formation of additional 2-methyl-2-butene from the other two isomers, so although the reactant to form isoprene may be the 2-methyl-2-butene isomer, it is possible for the other isomers to convert to 2-methyl-2-butene via an isomerization reaction and thereby become a reactant to form isoprene.

The term "regenerated catalyst" refers to a catalyst that has regained enough activity to be efficient in a specified process. Such efficiency is determined by individual process parameters.

The term "regeneration" refers to a process for renewing catalyst activity and/or making a catalyst reusable after its activity has reached an unacceptable/inefficient level. Examples of such regeneration may include passing steam over a catalyst bed or burning off carbon residue, for example.

The term "pentene" or "pentenes" refers to n-pentenes, or 1-pentene.

The term "piperylene" may also be referred to as 1,3-Pentadiene and Penta-1,3-diene 1-Mehylbutadiene.

Depending upon the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A method for the production of alkenes comprising:
   contacting a hydrocarbon feedstock with a dehydrogenation catalyst in a reactor, at a pressure of 1,000 mbar or less, under reaction conditions effective to dehydrogenate at least a portion of said hydrocarbon to produce alkenes;
   operating the dehydrogenation reaction at a steam to hydrocarbon molar ratio of at least 12:1; and
   operating the dehydrogenation reaction in a reactor at a temperature of at least 300° C.; and
   increasing a temperature of the reactor as needed to keep the hydrocarbon to alkene conversion at least 35%;
   wherein the hydrocarbon to alkene conversion is at least 30%;
   wherein the reactor temperature increase from catalyst deactivation averages no more than 1° C. per day for at least 30 days; and wherein the reaction can operate in excess of 30 days before the catalyst is a deactivated catalyst.

2. The method of claim 1, wherein the dehydrogenation catalyst has an average effective pore diameter of at least 500 nanometers.

3. The method of claim 1, wherein the dehydrogenation catalyst has ferric oxide as a major component and potassium as a lesser component.

4. The method of claim 1, wherein the dehydrogenation catalyst contains ferric oxide in amounts ranging from 40 wt % to 80 wt %, and potassium oxide or potassium carbonate in an amount of from about 5 wt % to 30 wt %.

5. The method of claim 1, further comprising:
   operating the dehydrogenation reactor at a pressure of 850 mbar or less; and
   increasing the reactor temperature as needed to keep the hydrocarbon to alkene conversion at least 40%.

6. The method of claim 1, further comprising:
   operating the dehydrogenation reactor at a steam to hydrocarbon molar ratio of at least 14:1;
   operating the dehydrogenation reactor at a pressure of 400 mbar or less; and
   increasing the reactor temperature as needed to keep the hydrocarbon to alkene conversion at least 40%.

7. The method of claim 1, further comprising:
   operating the dehydrogenation reactor at a steam to hydrocarbon molar ratio of at least 12:1;
   operating the dehydrogenation reactor at a pressure of 350 mbar or less; and
   increasing the reactor temperature as needed to keep the hydrocarbon to alkene conversion at least 40%.

8. The method of claim 1, further comprising:
   operating the dehydrogenation reactor at a steam to hydrocarbon molar ratio of at least 15:1;
   operating the dehydrogenation reactor at a pressure of 350 mbar or less;
   increasing the reactor temperature as needed to keep the hydrocarbon to alkene conversion at least 40%; and
   wherein the reactor temperature increase from catalyst deactivation averages no more than 0.5° C. per day.

9. The method of claim 1, wherein the reaction can operate in excess of 45 days before the catalyst is a deactivated catalyst.

10. The method of claim 1, wherein the reaction can operate in excess of 60 days before the catalyst is a deactivated catalyst.

11. The method of claim 1, wherein the hydrocarbon feedstock comprises 1-pentene and the reaction product comprises piperylene.

12. The method of claim 1, wherein the hydrocarbon feedstock comprises n-butane and the reaction product comprises butadiene.

* * * * *